United States Patent
Terry, Jr. et al.

(10) Patent No.: US 6,622,041 B2
(45) Date of Patent: *Sep. 16, 2003

(54) TREATMENT OF CONGESTIVE HEART FAILURE AND AUTONOMIC CARDIOVASCULAR DRIVE DISORDERS

(75) Inventors: Reese S. Terry, Jr., Houston, TX (US); Robert A. Adkins, Angleton, TX (US); Burke T. Barrett, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 59 days.

This patent is subject to a terminal disclaimer.

(21) Appl. No.: 09/933,086

(22) Filed: Aug. 21, 2001

(65) Prior Publication Data

US 2003/0040774 A1 Feb. 27, 2003

(51) Int. Cl.$^7$ .................................................. A61N 1/36
(52) U.S. Cl. ................................................ 607/9; 607/2
(58) Field of Search ................................. 128/897–898; 607/1–2, 4–5, 9, 14, 17, 19, 44, 115, 116, 118

(56) References Cited

U.S. PATENT DOCUMENTS

| | | | |
|---|---|---|---|
| 4,573,481 A | | 3/1986 | Bullara |
| 5,154,172 A | | 10/1992 | Terry, Jr. et al. |
| 5,304,206 A | | 4/1994 | Baker, Jr. et al. |
| 5,330,507 A | * | 7/1994 | Schwartz ..................... 607/14 |
| 5,707,400 A | * | 1/1998 | Terry et al. ................... 607/44 |
| 5,928,272 A | | 7/1999 | Adkins et al. |
| 6,002,963 A | * | 12/1999 | Mouchawar et al. .......... 607/18 |
| 6,006,134 A | * | 12/1999 | Hill et al. ....................... 607/9 |
| 6,073,048 A | * | 6/2000 | Kieval et al. ................. 607/17 |
| 6,141,590 A | * | 10/2000 | Renirie et al. ................ 607/20 |

* cited by examiner

Primary Examiner—Kennedy Schaetzle
Assistant Examiner—Kristen L Droesch
(74) Attorney, Agent, or Firm—Blank Rome LLP

(57) ABSTRACT

A device for treating patients suffering from congestive heart failure includes an implantable neurostimulator for stimulating the patient's vagus nerve at or above the cardiac branch with an electrical pulse waveform at a stimulating rate sufficient to maintain the patient's heart beat at a rate well below the patient's normal resting heart rate, thereby allowing rest and recovery of the heart muscle, to increase in coronary blood flow, and/or growth of coronary capillaries. A metabolic need sensor detects the patient's current physical state and concomitantly supplies a control signal to the neurostimulator to vary the stimulating rate. If the detection indicates a state of rest, the neurostimulator rate reduces the patient's heart rate below the patient's normal resting rate. If the detection indicates physical exertion, the neurostimulator rate increases the patient's heart rate above the normal resting rate.

24 Claims, 2 Drawing Sheets

TREATMENT OF CONGESTIVE HEART FAILURE AND AUTONOMIC CARDIOVASCULAR DRIVE DISORDERS

CROSS-REFERENCE TO RELATED APPLICATION

This application is related to application Ser. No. 09/417,080, filed Oct. 13, 1999, assigned to the same assignee as the present application, now U.S. Pat. No. 6,473,644, issued Oct. 29, 2002.

BACKGROUND OF THE INVENTION

It is currently estimated that some five million Americans suffer from congestive heart failure (CHF), a condition of abnormally low cardiac output. More than one million of these afflicted persons are under age 60. An increasing rate of CHF sufferers may be regarded as a sign of progress in the field of cardiology, since it stems in large measure from saving the lives of heart attack victims and patients with other heart problems. But many of the survivors are left with CHF, in which a markedly reduced cardiac output leads to an inability of the heart to maintain the body's need for oxygen-rich blood circulation. As many as 40 percent of CHF patients are at risk of sudden death.

Another fourteen million Americans are diabetic and forty million more exhibit hypertension (persistent elevated blood pressure). A considerable percentage of patients with diabetic neuropathy, hypertension and other pathologies affecting the nervous system are also at higher risk of sudden death.

Diseases such as CHF, hypertension and diabetes are characteristically associated with an increased autonomic cardiovascular drive (see, e.g., Blood Pressure 1998; Suppl 3:5–13). In addition, increased autonomic cardiovascular drive has been associated with myocardial infarction, cardiac transplantation, tetraplegia and anxiety disorders (Circulation 1996; 93:1043–1065, Bio Psychol March 1998; 47(3):243–63). "Tone" is the output that emanates from the central nervous system via sympathetic and parasympathetic efferent nerves. The overall "drive" depends on the balance between inhibitory (parasympathetic or vagal) and excitatory (sympathetic) tone and the responsiveness of the organ of interest to that tone. Responsiveness, in turn, depends on the receptor's properties as well as on the intrinsic functional or anatomic properties of the responding organ. An enhanced autonomic drive, independent of the underlying condition, greatly increases the risk of poor cardiovascular outcomes. It follows that targeting the underlying autonomic imbalance in congestive heart failure, hypertension and diabetes may not only be pathophysiologically sound but may also lead to better outcomes (Juilius, Blood Press 1998; Suppl 3:5–13).

As with any medical therapy, before a therapy is prescribed it is important to identify which patients are at increased risk. For CHF, research has established markers that identify patients at increased risk of sudden death from an imbalance between the sympathetic and parasympathetic systems. Results from a large multi-center trial established that baroreflex sensitivity and heart-rate variability are both predictors of mortality with CHF patients, and when combined, increase the predictive value (Lancet 1988:351:478–484). Similar studies have shown a predictive value of heart rate variability with diabetes (Circulation 1996;93:1043–1065).

The simplest measure of heart rate variability expresses the reciprocal of heart rate (R-R interval) and calculates a standard deviation of all normal beats (SDNN) over a period of time. The baroreflex sensitivity (BRS) is a marker of the capability to reflexly increase vagal activity and to decrease sympathetic activity in response to a sudden increase in blood pressure. It provides a more focused measure of autonomic control than heart rate variability. BRS is calculated from measurement of the rate-pressure response to intravenous phenylephrine.

Treatment strategies for CHF employ methods to decrease the excitatory or sympathetic drive, and/or to increase the inhibitory or parasympathetic drive. The results of clinical trials on two beta-blocker drugs demonstrate the efficacy of decreasing the sympathetic drive for such treatment. The clinical studies confirm earlier reports from dog study models of CHF treated with beta-blockers, that the drugs block the effects of adrenaline which is over-produced in CHF patients. Heart experts suspect that many symptoms of CHF occur as an overreaction of the body to some type of heart-muscle damage. The body misinterprets the situation and reacts as though severe dehydration or serious bleeding were the cause of the lowered blood flow. To stimulate the heart, the body produces more adrenaline, which makes the heart work harder. Deaths were reduced by 35% among patients given the beta-blockers Carvedilol or Metoprolol (Prog. cardiovascular Dis. January–February 1999; 41(4) 301–312, which states that beta-blockers should be considered the standard of care for mild-to-moderate heart failure). Unfortunately, beta-blockers—the older versions of which are relatively inexpensive—have side effects that prevent many patients from tolerating this mode of therapy.

Mild exercise has also been demonstrated to improve the sympathetic-parasympathetic balance for CHF patients. In a recent randomized study of 99 patients, Belardinelli reported (Circulation Mar. 9, 1999; 99(9):1173–1182) an 18% mortality in the exercise group compared to a 41% mortality in the non-exercise patient group. This clinical study confirms protective benefits of exercise training in dogs with simulated CHF (Circulation February 1994; 89(2):548552). Heart rate variability (SDNN) also improved by 74% in the dog study, suggesting an improved sympathetic-parasympathetic balance. Although beneficial, exercise is initially risky for the CHF patient until an improved balance of the sympathetic-parasympathetic system can be obtained. Exercise can trigger a heart attack or other adverse cardiac events in patients with unstable CHF. It is essential to monitor the patient closely during the first four to eight weeks of exercise. Even aside from the risk, initiating and maintaining an exercise program is difficult for CHF patients, because of patient fatigue and shortness of breath associated with the disease.

A cardiac defibrillator may be implanted to protect the CHF patient against sudden death upon an event of cardiac fibrillation, but its effect on long term survival is limited (Circulation Dec. 1, 1995; 92(11):3273–3281). The device (as well as the implant procedure) is relatively expensive, and does nothing to correct the underlining imbalance between the sympathetic and parasympathetic systems.

It is a principal aim of the present invention to provide improved methods of treating patients who suffer disorders as a result of increased autonomic cardiovascular drive, including but not limited to CHF, diabetes and hypertension. These improved methods seek to relieve the underlying autonomic imbalance between inhibitory (parasympathetic) and excitatory (sympathetic) tone.

SUMMARY OF THE INVENTION

The methods of this invention involve increasing the inhibitory response of the parasympathetic or vagal system.

The approach is to stimulate the cardiac branch of the vagus nerve. The protective role of vagal stimulation in the chronic dog CHF model has been reported (Circulation Research 1991;68:1471–1481). Prior to vagal stimulation, 100% of the dogs in the study were at risk of sudden death. After vagus nerve stimulation, only 10% remained at risk, versus 87% of a control group of dogs. The report states that the decrease in heart rate from vagal stimulation is an important but not always essential protective mechanism. The electrophysiological effects secondary to the vagally mediated antagonism of the sympathetic activity on the heart are likely to play a major role. In addition, vagal activity may have antagonized the vasoconstrictor effect of the sympathetic activity by acting on norepinephrine release and also by a direct vasodilatory effect.

Kamath reported on the neurocardiac responses to vagoafferent electrostimulation in eight patients with vagal stimulation for the control of epilepsy (Pace 1992, Vol 15, 1581–1587). These patients were chronically stimulated on the cervical branch below the cardiac branch; therefore, the effects are presumed to be central to the brain. The patients were randomized into High Level and Low Level stimulation groups. Those in the High Level stimulation group had a statistically significant improvement in the LF:HF peak power ratio (an expression of sympathetic dominance) as compared to the Low Level stimulation group, which had no improvement. Although slow and indirect response was elicited, these studies indicate that stimulation of the vagus nerve below the superior cardiac branch can have a long term beneficial effect on the balance of the sympathetic/parasympathetic system. The studies in dogs and humans demonstrate the feasibility of using vagus nerve stimulation to provide the heart with adequate parasympathetic support to promote natural healing.

The present invention, in one of its implementations, provides vagal stimulation to the left vagus nerve above the cardiac branch or on the vagus cardiac branch at a rate determined to limit the upper heart rate of the patient to a physiologically safe limit, such as 100–150 beats-per-minute (BPM). The stimulation is commenced whenever the BPM exceed a predetermined threshold, such as 90 BPM. The rate of cardiac vagus stimulation has an inverse effect on the heart rate. The stimulation rate may be experimentally determined and appropriately adjusted to achieve a particular heart rate for each patient during a treadmill test. For example, vagus nerve stimulation at 6 Hz may be determined to reduce the resting heart rate to 60 BPM. The physician might initiate the treadmill exercise and determine that by programming the vagus nerve stimulation rate to 4 Hz, the heart rate will be limited to about 100 BPM. Each of the vagal stimulation rates should be verified to assure that they do indeed result in the desired heart rate for each particular patient.

An alternative to the above method of limiting the upper heart rate is to sense the heart rate and to stimulate the vagus nerve only when the heart rate exceeds a specified threshold; for example, 100 BPM. Here again, the stimulation rate is experimentally determined by a treadmill test of the patient, to limit the heart rate to the 100–150 BPM range. Alternatively, the stimulation rate is automatically adjusted to maintain the rate within a specified range.

Another alternative method of the invention to limit upper heart rate is to synchronize the VNS to the P or R wave of the patient's EKG, and deliver a burst delayed from the synchronizing signal. The right vagus nerve is preferred for stimulation because it is more responsive to synchronized heart pacing, but the stimulation may be applied instead to the left vagus nerve. The burst is preferably approximately 100 msec in duration. The stimulation rate, burst duration, and delay from the synchronization point is programmed to limit the heart rate within a desired range; for example, 100 to 150 BPM. Exemplary values are VNS pulses delivered at a rate of 65 Hz, and the burst delayed 100 msec from the P wave. The heart rate should be monitored and burst mode parameters, specifically burst frequency, should be automatically adjusted to protect the patient from patterns which could produce a heart rate lower than desired.

The present invention provides left or right cardiac vagal stimulation at a rate determined to limit the heart rate 30–45% below the resting heart rate to allow the heart muscle additional time to rest and allow increased capillary blood flow and increased growth of capillary vessels. Since slowing the heart rate to allow time for the heart muscle to heal and to stimulate capillary growth will affect the patient's exercise tolerance (i.e., the exercise heart rate will be limited by the vagus stimulation rate), it is desirable to maximize the amount of time the heart rate can be slowed without impacting the patient's ability to function during normal daily activities. Preferably, then, the patient is stimulated only when at rest, and most preferably, when asleep. In any event, when a metabolic need for increased heart rate is indicated, the vagus stimulation is ceased or reduced sufficiently to allow the patient's normal heart rate to progress to within the upper rate limit range, such as to a programmed level of from 100 to 150 BPM. Of course, it will be understood that patients with CHF are not likely to be engaging in much, if any, strenuous activity.

Each of these methods should employ safety software to prevent stimulation at a frequency that reduces the heart rate below a physiologically safe level. The software should be designed to discriminate against electrical interference that might be interpreted as a fast cardiac signal. This type of discrimination is commonly used in implantable cardiac pacemakers and defibrillators. The VNS rate limit is tailored by programming for each individual patient.

The stimulator preferably incorporates a metabolic need sensor to detect a metabolic need for increased blood flow through higher heart rate. Examples of a suitable sensor include an activity sensor to detect physical activity by the patient (such as an accelerometer), an $O_2$ saturation sensor, a temperature (central venous blood, or physiology) sensor, a respiration (or minute ventilation) rate sensor, a Q-T interval sensor, and so forth. The metabolic need sensor is arranged and adapted to inhibit or otherwise control the vagus stimulation rate to avoid limiting the heart rate to an inappropriately low level in circumstances of patient exercise or activity, which may even be very slight such as getting up from a chair or slow walking. Alternatively or additionally, the stimulator may be programmed to adjust the target heart rate to a higher ventricular rate upon sensing patient activity, so the patient will receive the benefit of a higher heart rate under conditions of exercise.

Subject to approval by the physician, and appropriate programming, the patient may be given some limited control over the therapy. To that end, an external magnet may be made available to the patient to allow initiating stimulation or inhibiting stimulation. The impanted device may be programmed to assume a different heart rate target when activated by a magnet.

Also, the device may be programmed to commence different heart rate targets during local daytime and nighttime hours.

BRIEF DESCRIPTION OF THE DRAWINGS

The above and other aims, objectives, aspects, features and attendant advantages of the invention will be further understood from a reading of the following detailed description of the best mode presently contemplated for practicing the invention, taken with reference to certain presently preferred implementations and methods, and in conjunction with the accompanying drawings, in which.

DETAILED DESCRIPTION OF BEST MODE PRESENTLY CONTEMPLATED TO PRACTICE THE INVENTION

Figure 1:
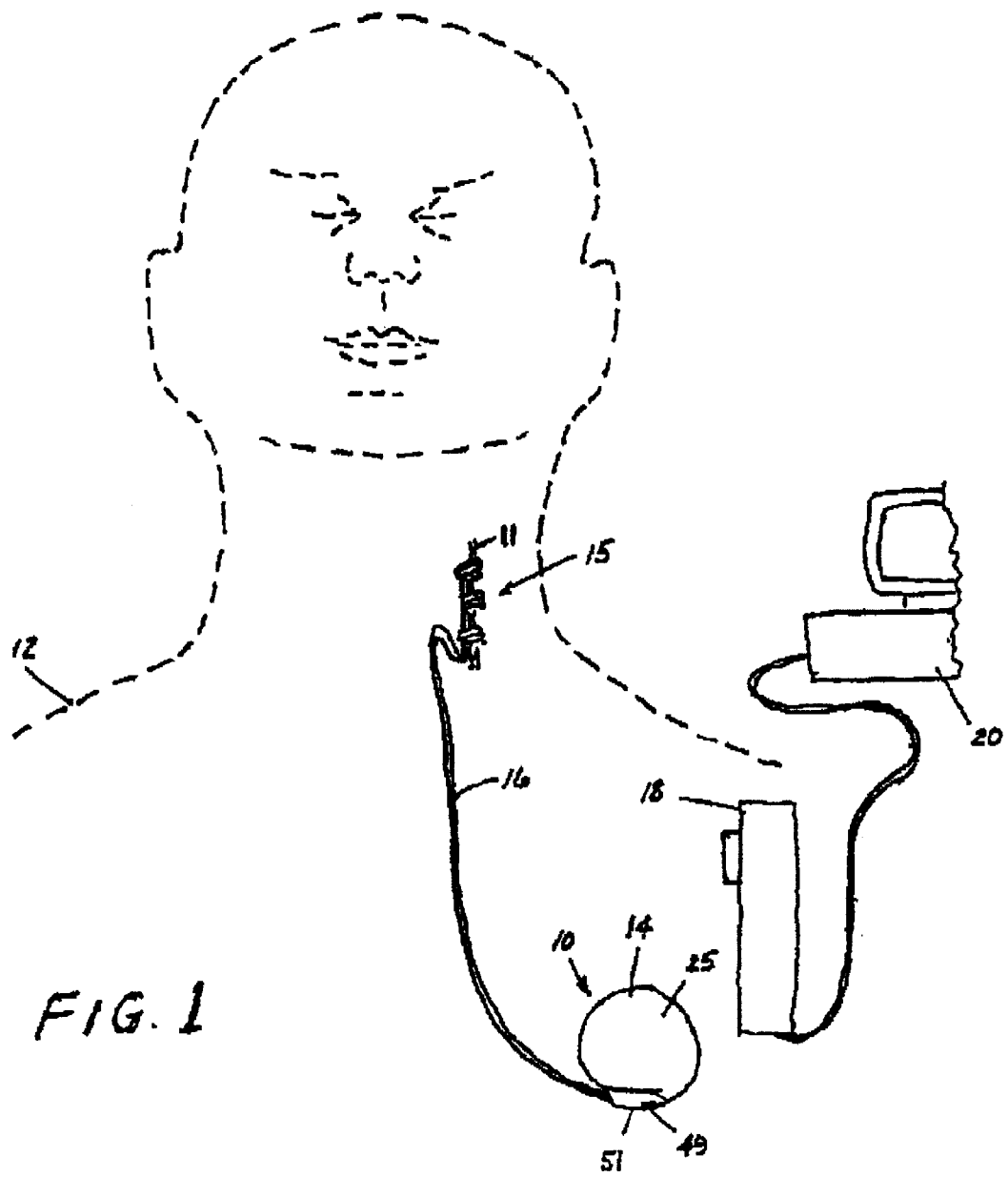
FIG. 1 is a simplified diagram of a neurostimulator device with associated lead-electrode system implanted in a patient's body.

In FIG. 1, a patient 12 (illustrated in phantom) has an implanted neurostimulator device 10 which may be of the type disclosed in U.S. Pat. No. 5,154,172 to R. S. Terry, Jr. et al., assigned to the assignee of the present application, except with respect to certain improvements according to the present invention as described below. The signal generator or stimulus generator 25 of device 10 is sometimes referred to herein as a NeuroCybernetic Prosthesis orNCP® (registered trademark of Cyberonics, Inc., the assignee herein) prosthetic device.

The housing 14 (generally referred to in the art as a "can" or "case") of the stimulus generator 25 is composed of biocompatible material, e.g., a metal such as titanium or medical grade stainless steel, hermetically sealed to prevent fluid penetration into the electronic components and battery (ies) (sometimes referred to herein as the "electronics package") contained therein. Case 14 has a thin circular, oval, or rectangular shape and is suitably sized for implantation. The device is implanted in a surgically-formed pocket just below the skin, typically in a pectoral region of the patient. An insulated, electrically conductive lead 16 is connected at its proximal end to generator 25 and at its distal end to an electrode array 15 which is to be installed on the right or left branch of the vagus nerve 11, above the cardiac branch. The right vagus electrode placement is believed to be more responsive to synchronized burst stimulation, discussed below, but left vagus stimulation may alternatively be used.

A connector at the proximal end of lead 16 is inserted into a mating connector in header 51 on case 14, to electrically connect the electrode array 15 to the electrical circuitry of the electronics package in the stimulus generator 25. For example, the electrode array may be a bipolar stimulating electrode assembly as shown in U.S. Pat. No. 4,573,481 to Bullara. The electrical output pulse waveform of generator 25 is applied through the lead-electrode system to the vagus nerve at a desired location, such as the cervical location shown in FIG. 1.

Telemetry communication with the implanted stimulus generator for programming and monitoring purposes is performed using a program console external to the patient's body, by asynchronous serial communication. For example, a programming wand 18 is used to transmit parameter changes to device 10 and to receive device parameter and signal information being monitored, in conjunction with computer 20 of the program console. Software installed in the computer facilitates physician-controlled adjustment of selected parameters and communication with the implanted device. An antenna 40 (FIG. 2) within the generator is used for bidirectional telemetry communication between the implanted device and the external program console, via wand 18.

Figure 2:
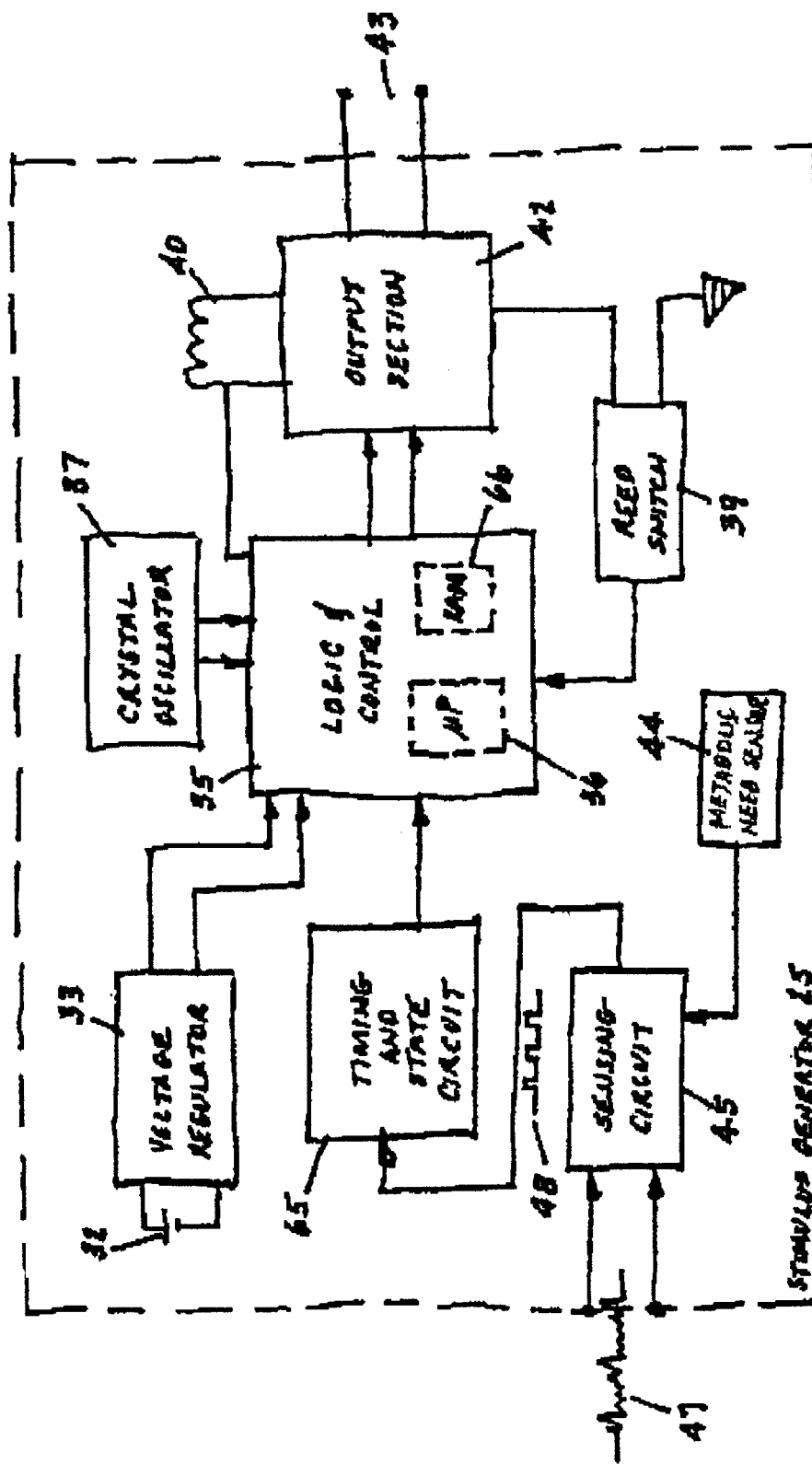
FIG. 2 is a simplified block diagram of an implantable stimulus generator of a type used in the device of FIG. 1 to trigger VNS according to the present invention.

FIG. 2 illustrates a simplified block diagram of NCP stimulus generator 25, including battery(ies) 32 (e.g., a lithium carbon monofluoride cell) which, together with a voltage regulator 33, powers the implanted device, and a logic and control section 35 with a microprocessor 36 that implements and controls the programmable functions of the device. These functions include sensing and stimulation control parameters for the stimulus generator for receipt from or application to lead 16 and distal electrode array 15 in communication from or to vagus nerve 11, as the case may be. The attending physician programs the implanted device to selectively tailor the output pulse waveform of the generator to stimulate or modulate the electrical activity of the vagus nerve for a prescribed therapy regimen for treatment of a patient's autonomic cardiovascular drive disorders by decreasing autonomic nervous system drive. Once the generator is programmed, it operates at the programmed settings until they are re-programmed by the attending physician.

Timing of the logic and control and other functions of the stimulus generator is controlled by a precise signal frequency of a crystal oscillator 37. A magnetically-actuatable reed switch 39 is provided to allow physician-prescribed limited manual activation by the patient of certain functions of the generator with an external magnet (not shown). Alternatively or additionally, the implanted device may be implemented to use techniques of manual and automatic activation disclosed in U.S. Pat. No. 5,304,206 to R. G. Baker, Jr. et al., assigned to the same assignee as the present application. For example, the patient may be allowed to initiate delivery of the output pulse waveform to adjust the stimulation frequency to increase the heart rate during periods of physical activity by the patient, or to reduce the heart rate toward the lower target range when the activity has ceased for a sufficient interval, as noted above in the brief summary of the invention. Manual control may also be used to inhibit stimulation if the patient experiences discomfort with the programmed therapy or in the event of a perceived malfunction.

Logic/control section 35 controls output circuit 42 for producing the output pulse waveform according to the prescribed therapy. The stimulus generator may be programmed for continuous, periodic or sporadic activation of programmed operation as necessary to bring the patient's detected ventricular rate to a target level stored in a comparator. The ventricular rate is monitored by input signal 47 to sensing circuit 45, which delivers a proportional pulse output to timing and state circuit 65. The output of the latter is applied to logic and control circuit 35 to initiate and/or adjust the VNS frequency or rate for proper autonomic nervous system drive.

Techniques for sensing heart rate from the vagus nerve electrode are disclosed in U.S. Pat. No. 5,928,272 to A. Adkins et al, assigned to the same assignee as the present application. The generator 25 is programmed to stimulate the vagus nerve at an initial pulse stimulation frequency, and, when the patient's heart rate begins to move toward the prescribed target rate, to enter into the specified therapy regimen. For certain of the techniques described herein, the generator cannot be used to sense and stimulate from the same nerve electrode, but requires a distinct sensing electrode to avoid missing an event while pulses are being delivered. A separate electrode for sensing may be incorporated as an integral part of the pulse generator, for example at on the header. Alternatively, a separate lead could be used with the sense tip positioned away from the stimulating electrode. Although not required, the sensing tip could be positioned in, or in close proximity to, the heart. This could also be implemented with one lead body, with a ring sense electrode located around the lead body some distance from the stimulation site. However, if the generator is used exclusively in the synchronous burst mode (described below), a separate sensing electrode is not required and the nerve electrode may be used for sensing.

A technique employed in the invention is to increase the inhibitory response of the parasympathetic or vagal system (decrease the autonomic nervous system drive) by appropriate stimulation of the cardiac branch of the vagus nerve. In one method, the vagus nerve (left or right branch in the cervical region above the cardiac branch) is stimulated by the generator pulse waveform at a rate which is predetermined to limit the particular patient's upper heart rate to a physiologically safe limit within a prescribed range, e.g., 100–150 BPM. The stimulation rate is experimentally determined during treadmill testing of the patient. Typically, a vagus nerve stimulation rate of about 4 Hz limits the heart rate to about 100 BPM. Since the heart rate varies inversely with the VNS rate, lower stimulation rates produce proportionally higher heart rate limits. In an alternative method, heart rate is monitored and VNS is applied only when the heart rate is detected to fall below a threshold such as 100 BPM. Another alternative is to use feedback to automatically adjust the vagal stimulation rate to maintain the heart rate within the desired range.

It is important to stimulate the vagus nerve above the cardiac branch, since stimulation of the main branch of the vagus in the neck below the cardiac branch will not affect the heart rate. The cardiac cervical branch of the vagus nerve provides the most convenient access location for attaching the electrode, as it branches from the main trunk of the vagus relatively high in the neck, thus providing a sufficiently long section in the neck for electrode attachment. Stimulation of either the left vagus nerve or the right vagus nerve is acceptable.

In another method of adjusting autonomic nervous system drive according to the invention, the VNS may be synchronized to the P wave or R wave of the patient's EKG to time delivery of a pulsed burst from the generator with a predetermined time delay from the synchronizing signal. For example, the burst may commence about 150 to 200 msec after the R wave. An advantage of this method is reduced power (battery) consumption, owing to a lower stimulation duty cycle. The stimulation rate, burst duration (e.g., 100 msec), and time delay (e.g., 100 msec) from the P wave, are programmed to limit the heart rate to a value within the prescribed range of about 100 to 150 BPM. An amplifier may be employed to sense the presence of a P wave, indicating atrial contraction, and an electrode inserted in the atrium for increased sensitivity to P wave signal amplitude. A single amplifier-electrode device with a signal analyzer to differentiate between the P wave and the R wave may be used as an alternative.

The burst mode is programmed with limits on burst frequency, duration, and repetition rate to avoid very low heart rates that can compromise physical performance. But the other methods require similar procedures for the sake of safe treatment of the patient. For example, the software should be designed to place limits on minimum and maximum stimulation rates to avoid very high and very low heart rate levels, as well as to discriminate against improper interpretation of electrical interference as a cardiac signal (commonly employed in implantable cardiac pacemakers and defibrillators). Noise detection algorithms may be used, and when noise is detected the vagus nerve stimulation is automatically inhibited.

For a patient suffering from CHF, heart rate is preferably reduced to within a rate range below (preferably, 10 to 45% below, and more preferably, 30 to 45% below) the low end of the normal resting rate range of the patient. The intent is to provide a longer resting period for the heart muscle between beats and promote additional coronary flow and capillary development. In this regimen, the vagal stimulation frequency may be automatically adjusted as a function of the difference between the actual ventricular rate and the target rate. At the commencement of stimulation, the vagus nerve is subjected to stimulation at a frequency, for example, of one pulse per second. This stimulation frequency is sustained for a specified but relatively brief interval of time, e.g., about one minute, to allow the ventricular rate to stabilize at a new level. The vagal stimulation frequency may then be increased to a level of about two pulses per second, and again, held until the ventricular rate stabilizes. This regimen is continued with further increase in vagal stimulation frequency for each measurable reduction in the heart rate and subsequent stabilization interval, until the ventricular rate reaches the prescribed target rate.

Preferably, the rate of change of increase in the vagal stimulation frequency is programmed according to the therapy regimen to decline to 0.5 pulse per second between successive stabilization intervals, for example, from the prior one pulse per second, as the ventricular rate approaches the target rate range. Alternatively, the controller may take the percentage of difference between the desired and actual ventricular rate, multiplied by a constant factor, and add to the vagus stimulation rate, to achieve a modified vagal stimulation rate by which the heart rate approaches the target rate. The vagus stimulation frequency is increased to lower the ventricular rate towards the desired range, so long as the atrial-ventricular synchrony is present, but if such synchrony is lost the ventricular rate is held in a range just above the rate at which that occurred.

Lowering the patient's heart rate to a ventricular bradycardia in a range of from about 30% to 45% of the baseline resting heart rate, or about 38 BPM to 49 BPM for a resting rate of 70 BPM, is anticipated to promote and enhance the growth of coronary blood vessels, and especially the myocardial capillaries, to provide an increase in coronary blood flow through the heart. And cardiac output is expected to improve gradually over a period of several weeks or longer as a result of increase in the capillaries and the coronary blood flow.

Safeguards should be provided here, also, to prevent inadvertent reduction of the patient's heart rate stemming from electrical noise interference. To that end, a noise rejection algorithm may be used as noted earlier herein, and, additionally, the device is preferably programmed with a maximum vagal stimulation rate that establishes a physiologically safe heart rate lower limit for the patient.

In an alternative therapy protocol, the implanted neurostimulator may be programmed to undergo much less frequent changes, so that the patient's heart rate is reduced periodically and held at the reduced level. To that end, the vagal stimulation rate is increased and held, e.g., for a period of, say, one hour to produce an interim designated ventricular rate. At the end of the one-hour period, the vagal stimulation is ceased or adjusted to a lower frequency for a period of one hour to allow the heart rate to return to and remain at the patient's normal resting rate. The periods of stimulation and non-stimulation (or adjusted stimulation) are sufficient and nominally (but not necessarily) of the same or similar lengths of time, to provide a desirable protocol in circumstances where the patient is unable to tolerate a protracted reduced heart rate.

Severe bradycardia lowers cardiac output in patients as stroke volume falls, especially patients with other underlying heart disease. Aerobic exercise capacity is also impaired in CHF patients. Of course, reducing the heart rate exacerbates that condition. Patient exercise, if tolerated at all, is beneficial because it promotes increased capillary growth and coronary blood flow, so it is desirable to allow the patient to engage in some moderate exercise.

A metabolic need sensor 44 among the examples of suitable sensors noted earlier herein is used to detect physical exertion by the patient, and in response to initiate an inhibition of VNS that would otherwise limit heart rate to an inordinately low level for those conditions. The metabolic need sensor may alternatively or additionally be used to change the vagal stimulation to a rate that allows an increase in the patient's ventricular rate above the predetermined rate upon sensing patient activity. For example, the heart rate might normally be limited to 100 BPM by vagal stimulation, but when exercise is detected the vagal stimulation rate may be decreased to allow the heart rate to increase to as much as 150 BPM.

Even mere changes in position or slow walking are detected by the metabolic need sensor to trigger either an inhibition of the vagal stimulation, or an adjustment of the vagal stimulation frequency to allow an intrinsic higher ventricular rate, with limits on the increase in heart rate to a safe level. Consequently, the patient receives the benefit of a more physiologically appropriate higher heart rate at least during a period of physical activity and receives protection from abnormally high heart rates which could result in tachycardia or sudden death. When the patient returns to a resting condition, the absence of activity (or intrinsic fallback of the heart rate) is detected by the metabolic need sensor.

A damped feedback loop with hysteresis can be used to maintain the frequency of stimulation of the vagus nerve at a level sufficient to substantially sustain the ventricular rate within a target rate range. Damped feedback makes small or proportionately small changes in the stimulation rate to increase or decrease the heart rate into the desired range. Damping should be provided while increasing the VNS frequency to reduce the heart rate, whereas it is preferred for safety reasons that no damping be employed while decreasing the vagal stimulation frequency to allow an increase in the heart rate when it is too low.

According to another aspect of the invention, the device may be programmed for some patients to undergo vagal stimulation at different target heart rates according to the time of day (e.g., differently during daytime and nighttime hours), or otherwise according to the circadian rhythm of the patient, such as is appropriate to a lower heart rate during sleep or slumber than during the patient's waking hours. This implementation may be achieved in part through the incorporation of a time-of-day clock beyond the clocking provided for operation of the electronics package of the device. The programming for such selected patients may allow a reduction in the target rate during the nighttime hours. However, since the sleep time of individual patients varies, and patients may be expected to travel to different time zones, a more preferred implementation uses a metabolic need sensor. The sensor simply detects the patient's metabolic need and adjusts the rate accordingly. A sophisticated algorithm is not required, but merely two rates—a resting heart rate and a non-resting heart rate.

The times (i.e., intervals) during which the implanted device is activated for stimulation of the vagus nerve to lower (or raise) the heart rate and inhibited (or the stimulation is decreased sufficiently) to return the heart rate back toward the normal (for the particular patient) resting level may be programmed from a range of minutes to hours or even days in length. Also, the implanted device is preferably implemented to detect a heart rate that falls below the prescribed target rate, and to respond by an automatic reduction of the vagal stimulation frequency or cessation of the stimulation entirely, at least until a recovery to that target rate is detected.

Although the invention has been described with respect to treatment of CHF patients by relieving the underlying autonomic imbalance between inhibitory (parasympathetic) and excitatory (sympathetic) tone, by increasing the inhibitory response of the parasympathetic or vagal system through stimulation of the cardiac branch of the vagus nerve, other disorders such as diabetes and hypertension can also be treated by similar techniques of reducing the autonomic nervous system drive.

From the foregoing description, it will be seen that vagus stimulation for the treatment of CHF can accomplish several clinical objectives, although stimulation parameters may need to be changed for specific outcomes. Stimulation of the vagus above the cardiac branch at a rate sufficient to lower the resting heart rate by a specified percentage, such as 10%–45%, is contemplated to be helpful to allow more time for the heart muscle to repair during muscle contractions. This method is also contemplated to be beneficial in stimulating the growth of additional coronary capillaries, which will supply more blood to the heart muscle. Still further, the method may also be beneficial in dilating the coronary vessels and increasing coronary blood flow, which would aid in recovery and strengthening of the heart muscle.

Since the stimulation lowers the heart rate, it also lowers the immediate exercise tolerance of the patient. Therefore, it is advisable to program this therapy to occur only at night or other times during the day when the patient is resting. Preferably, a metabolic need sensor (which could be a motion sensor, an accelerometer or any of a variety of other detectors of physical exercise, the most preferred being those that are simple and effective, e.g., combined within the stimulator itself and not otherwise invasive) may be incorporated in or with the implanted device to sense exercise and disable this mode of therapy during exercise.

Stimulation to limit the heart rate to some prescribed percentage increase above the resting heart rate is a mode of therapy whose purpose is to improve the vagal tone or the balance between the sympathetic and parasympathetic systems. The clinical outcome is to assist the cardiac system to remain in a state of control, rather than reaching a lack of control which can lead to tachycardia, fibrillation and sudden death. This approach should be differentiated from that of defibrillators, which stop the fibrillation but do nothing to help the body reach a better state of control; and differentiated from that of using vagal stimulation to limit the upper heart rate for preventing tachycardia. Direct stimulation of the cardiac branch is believed to have the greatest immediate effect, although stimulation of the cervical vagus nerve also improves the LF:HP peak power ratio, an expression of sympathetic dominance.

A technique which delivers a burst of pulses, synchronized with and delayed from the QRS may be the preferred method.

Techniques for adjusting stimulation patterns may be dependent on the clinical outcome. For example, if the objective is to lower the resting heart rate, the clinician would just measure heart rate. If the objective were to limit the upper heart rate to improve sympathetic/parasympathetic stability, the adjustment may need to be made while the patient is exercising, such as on a treadmill. Alternatively, the heart rate variability and specifically the LF:HF peak power ratio or some other specific parameter associated with sympathetic/parasympathetic balance could be measured. These parameters may not respond immediately and stimulation parameters may need to be adjusted over a period of weeks or months to achieve the desired improvement.

Automatic sensing of metabolic need indicated by way of physical activity may be incorporated into these methods and programmed by the physician to allow the patient some degree of heart rate increase during physical exercise. Timers alone could be used for fixed period of exercise, whereas a motion sensor or activity sensor such as an accelerometer may be used for automatic detection of patient activity. The patient might also be provided with a patient activation mechanism of a type described herein to permit increased heart rate.

Typically, the electrode for vagal stimulation is installed on or at the vagus nerve above the cardiac branch or directly on the cardiac branch, usually in the neck area. If the electrode is installed below the cardiac branch, the stimulation does not have a direct effect on the heart rate, but may improve the autonomic system balance.

Although a presently contemplated best mode of practicing the present invention has been disclosed herein by reference to certain preferred methods and embodiments, it will be apparent to those skilled in the field of the invention from a consideration of the foregoing disclosure that variations and modifications may be made without departing from the spirit and scope of the invention. Accordingly, it is intended that the invention shall be limited only to the extent required by the appended claims and the rules and principles of applicable law.

What is claimed is:

1. A method of treating patients suffering from congestive heart failure (CHF), which comprises identifying a CHF patient, and reducing the heart rate of the identified patient by vagus stimulation to a rate below the low end of the patient's resting rate range, to rest the heart, promote growth of coronary capillaries, and to increase coronary blood flow.

2. A method of treating a patient suffering from congestive heart failure, which comprises the steps of:
   electrically stimulating the patient's vagus nerve at or above the cardiac branch while the patient is at rest to reduce the patient's heart rate to a prescribed target rate below the patient's normal resting heart rate; and
   continuing said electrical stimulation of the vagus nerve to maintain the patient's heart rate substantially at said prescribed target rate for a predetermined portion of the period the patient remains at rest.

3. The method of claim 2, including using an implanted programmable neurostimulator to perform the electrical stimulation of the patient's vagus nerve.

4. The method of claim 3, including applying said electrical stimulation to an electrode installed on a branch of the vagus nerve in the patient's neck.

5. The method of claim 2, including performing said electrical stimulation using an electrical pulse waveform.

6. The method of claim 5, including applying a pulse burst synchronized with the P wave or R wave of the patient's cardiac activity.

7. The method of claim 2, including
   detecting the patient's metabolic need, and
   ceasing or adjusting said electrical stimulation when the detected metabolic need mandates a heart rate higher than the patient's normal resting rate.

8. The method of claim 7, including using an activity sensor to detect the patient's metabolic need.

9. The method of claim 8, including using an accelerometer as said activity sensor to detect the patient's metabolic need.

10. The method of claim 2, including continuing said electrical stimulation of the vagus nerve to maintain the patient's heart rate substantially at said prescribed target rate in a lower heart rate limit range of from 10% to 45% below the patient's normal resting heart rate.

11. The method of claim 2, including continuing said electrical stimulation of the vagus nerve to maintain the patient's heart rate substantially at said prescribed target rate for the entire period the patient remains at rest.

12. The method of claim 2, including continuing said electrical stimulation of the vagus nerve to maintain the patient's heart rate substantially at said prescribed target rate during the normal sleep time according to the patient's circadian rhythm.

13. The method of claim 5 including adjusting the stimulation frequency of the pulses while the heart rate is declining, to reduce the rate at which the patient's heart rate approaches said prescribed target rate.

14. The method of claim 2, including permitting limited patient control of said electrical stimulation of the patient's vagus nerve.

15. A method of treating a patient suffering from autonomic cardiovascular drive disorder, which comprises the steps of electrically stimulating the patient's vagus nerve at or above the cardiac branch with a pulse waveform delivered at an appropriate stimulation rate determined by subjecting the patient to an exercise test, to adjust the patient's heart rate to a physiologically safe target rate in a prescribed upper heart rate limit range above the patient's normal resting heart rate, and monitoring the patient's heart rate to ascertain when it is within said prescribed upper heart rate limit range.

16. The method of claim 15, including using an implanted programmable neurostimulator to perform the electrical stimulation of the patient's vagus nerve.

17. The method of claim 16, including applying said electrical stimulation to an electrode installed on a branch of the vagus nerve in the patient's neck.

18. The method of claim 15, including prescribing said upper heart rate limit range from about 100 BPM to about 150 BPM.

19. The method of claim 15, including performing said electrical stimulation of the vagus nerve only when the patient's heart rate is detected to be below the lower limit of said prescribed upper heart rate limit range.

20. The method of claim 15, including performing said electrical stimulation of the vagus nerve by applying a pulse burst synchronized with the P wave or R wave of the patient's cardiac activity.

21. The method of claim 15, including using a feedback loop to automatically adjust the vagal stimulation rate to maintain the patient's heart rate within said prescribed upper heart rate limit range.

22. The method of claim 15, including determining said appropriate stimulation rate by subjecting the patient to a treadmill test.

23. The method of claim 15, including using a metabolic need sensor to refine said physiologically safe target rate according to physical exertion of the patient.

24. The method of claim 15, including enabling the patient to adjust the heart rate limit within a prescribed range having an upper limit lower than the upper limit of said prescribed upper heart rate limit range.

* * * * *